United States Patent [19]
Cowherd, III

[11] Patent Number: 4,568,746
[45] Date of Patent: Feb. 4, 1986

[54] CATALYTIC PREPARATION OF DIETHYLENETRIAMINE

[75] Inventor: Frank G. Cowherd, III, Charleston, W. Va.

[73] Assignee: Union Carbide Corporation, Danbury, Conn.

[21] Appl. No.: 454,485

[22] Filed: Dec. 29, 1982

[51] Int. Cl.$^4$ .................... C07D 241/04; C07C 87/20
[52] U.S. Cl. .................................... 544/358; 564/461; 564/479; 564/480
[58] Field of Search ................ 544/358; 564/461, 479, 564/480

[56] References Cited

U.S. PATENT DOCUMENTS

| | | | |
|---|---|---|---|
| 2,781,399 | 6/1956 | Mannheimer | 260/458 |
| 2,861,995 | 11/1958 | MacKenzie | 544/358 |
| 3,068,290 | 7/1958 | Lichtenberger | 260/585 |
| 3,714,259 | 1/1973 | Lichtenwalter | 564/480 |
| 4,036,881 | 7/1977 | Brennan et al. | 564/479 |

FOREIGN PATENT DOCUMENTS 1508460 4/1978 United Kingdom.

OTHER PUBLICATIONS

*Chem. Abstracts*, vol. 59, No. 3, 2813d (Aug. 5, 1963), "Catalytic Deamination of W, W'-Diamines by Raney Nickel Catalysts".

*Primary Examiner*—George F. Lesmes
*Assistant Examiner*—S. A. Gibson
*Attorney, Agent, or Firm*—Steven T. Trinker

[57] ABSTRACT

A process for the production of an amine composition with a high proportion of diethylenetriamine to piperazine comprising reacting ethylenediamine with itself or monoethanolamine in the presence of a nickel, cobalt or rhodium catalyst at temperatures between about 170° C. and 210° C.

12 Claims, 1 Drawing Figure

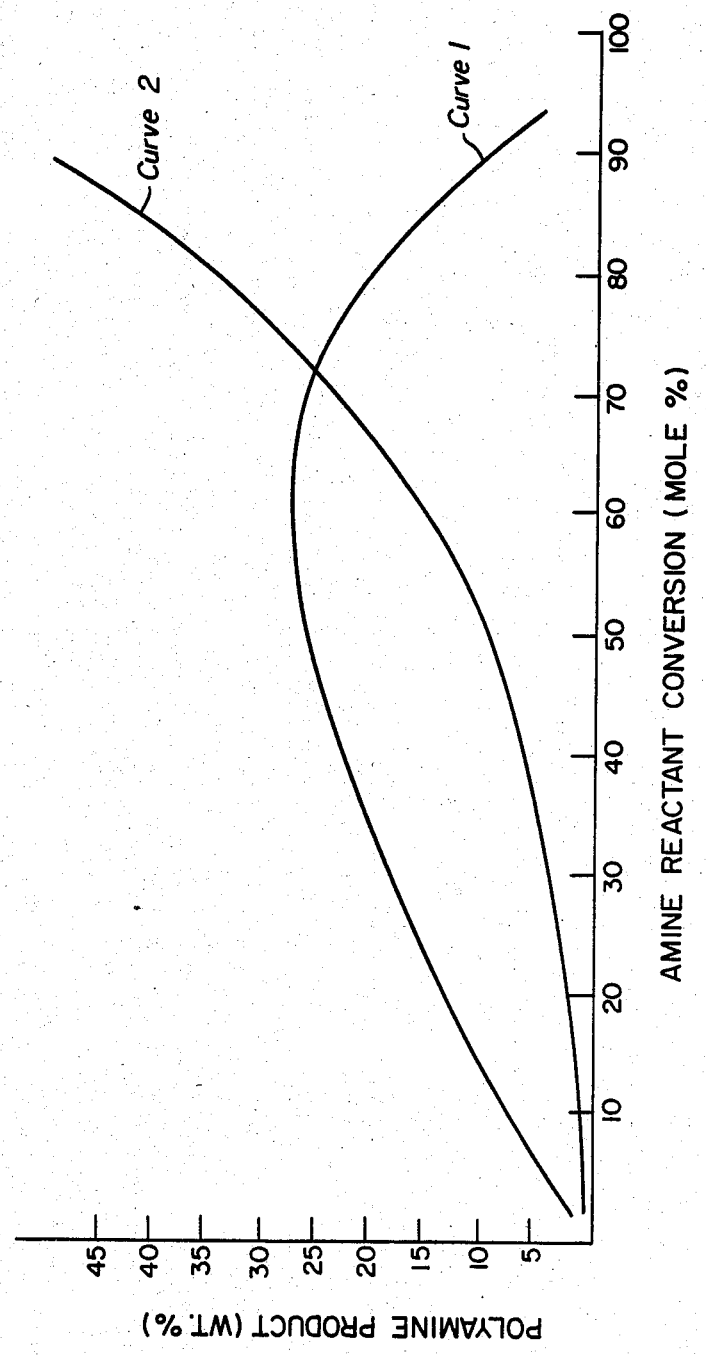

4,568,746

CATALYTIC PREPARATION OF DIETHYLENETRIAMINE

TECHNICAL FIELD

The present invention relates to the reaction of a lower molecular weight polyamine to form a lower molecular weight, linear, polyalkylene polyamine.

BACKGROUND OF THE INVENTION

Low molecular weight linear polyalkylene polyamines are known for their many uses in industry. For example, U.S. Pat. No. 2,781,389 to Mannheimer discloses the use of such linear polyalkylene polyamines to form detergent sulfonic acids and sulfate salts of ampho- teric detergents.

U.S. Pat. No. 2,781,389 discloses that such linear polyalkylene polyamines can be produced by reacting ethylene oxide with ammonia. The patent fails to disclose any operable reaction conditions or useful catalysts for such a reaction. U.S. Pat. No. 3,068,290 to Lichtenberger discloses that monoethanolamine may be treated with ammonia at elevated temperatures in the presence of a Raney Ni catalyst to produce an amine composition that is composed mainly of the monoalkylene polyamine, ethylenediamine, but which does contain some polyalkylene polyamines, e.g., diethylenetriamine and piperazine, in roughly equal minor amounts. The prevalent commercial process for producing ethylenediamine from monoethanolamine produces roughly equal minor amounts of diethylenetriamine and piperazine as components of a complex mixture of polyethylene polyamines which is then distilled to obtain the components in a purified form.

Because a linear polyalkylene polyamine such as diethylenetriamine and a cyclic polyalkylene polyamine such as piperazine do not have the same industrial uses and demands, it has been recognized that it would be desirable to develop a process with sufficient selectivity in forming a linear polyalkylene polyamine to produce an amine composition with a relatively high ratio of diethylenetriamine to piperazine. For example, U.S. Pat. No. 4,036,881 discloses that a phosphorous-containing compound will catalyze the reaction of ethylenediamine with monoethanolamine at temperatures between 250° C. and 350° C. to yield an amine composition that may have a high ratio of diethylenetriamine to piperazine. However, the high temperatures and pressures employed in U.S. Pat. No. 4,036,881 may be undesirable in a given process stream.

Processes which produce amine compositions at temperatures lower than those in U.S. Pat. No. 4,036,881 are described in U.S. Pat. No. 3,714,259 to Lichtenwalter et al. and British Pat. No. 1,508,460 to BSAF Aktiengesellschaft. U.S. Pat. No. 3,714,259 discloses that ethylenediamine will react with monoethanolamine in the presence of a nickel, copper, iron, palladium, platinum, cobalt, chromium, rhodium, molybdenum or titanium catalyst at between 140° C. to 170° C. and pressures ranging from 200 to 5000 psig of hydrogen. British Pat. No. 1,508,460 discloses that ethylenediamine will react with itself at a temperature between 100° C. and 150° C. in the presence of iron, nickel, cobalt, palladium, rhodium, ruthenium, or platinum. However, British Pat. No. 1,508,460 also discloses that the narrow temperature range of 100° to 150° is critical because the main product above 150° C. is the cyclized polyalkylene polyamine, piperazine, rather than the linear polyalkylene polyamine, diethylenetriamine. It has also been found that a number of the catalysts disclosed by British Pat. No. 1,508,460 and U.S. Pat. No. 3,714,259 are practically inoperable at about 200° C., i.e., produced conversion rates less than 5%, at about 200° C. Moreover, the highest weight ratio of diethylenetriamine to piperazine disclosed by U.S. Pat. No. 3,714,259 is 4.5:1 with an average ratio of 3.16:1.

SUMMARY OF THE INVENTION

In accordance with the present invention, there is provided a process for the production of an amine composition having a high ratio of diethylenetriamine to piperazine which comprises maintaining ethylenediamine in the presence of a catalyst selected from the group of nickel, cobalt or rhodium, wherein the metal is present on the surface of the catalyst in a polyatomic form, and at a temperature between about 170° C. to about 210° C. sufficient to convert less than about 35% of the amine reactants to polyamine.

Also provided in a process for the production of an amine composition having a high ratio of diethylenetriamine to piperazine which comprises maintaining a mixture of ethylenediamine and monoethanolamine in the presence of nickel, cobalt or rhodium, wherein the metal is present on the surface of the catalyst in a polyatomic form, and at a temperature between about 170° C. and about 210° C. sufficient to convert less than about 35% of the amine reactants to polyamine.

BRIEF DESCRIPTION OF DRAWING

The drawing is a graphical representation of the amounts of diethylenetriamine and piperazine in a typical product mixture produced by the practice of the instant invention. The percentage by weight of each product is plotted against the amount of amine reactants converted at a given time. Curve 1 is the percentage of diethylenetriamine and Curve 2 is the percentage of piperazine.

DETAILED DESCRIPTION OF THE INVENTION

It has now been found in accordance with the present invention that the reaction of ethylene-diamine with itself or with monoethanolamine in the presence of a nickel, cobalt or rhodium catalyst to form ammonia and a polyalkylene polyamine can be controlled so as to maximize the amount of the linear polyalkylene polyamine, diethylenetriamine, that is formed with respect to the amount of the cyclized polyalkylene polyamine, piperazine, that is formed.

The reaction is thought to proceed by the reaction of ethylenediamine with itself or monoethanolamine to form diethylenetriamine and a molar equivalent of ammonia or water. The nickel, cobalt or rhodium catalyst used to facilitate such a reaction will also catalyze the cyclization of diethylenetriamine to form piperazine and another equivalent of ammonia. Whether the reaction mixture will contain a high ratio of linear to cyclized polyamine is a function of the reaction rates of forming a linear polyalkylene polyamine and the reaction rates of forming a cyclized polyamine from the linear polyamine. The reaction rate of the three reactions are of course dependent upon the catalyst chosen and the temperature at which the reaction mixture is maintained. It has been found that when a nickel, cobalt or rhodium catalyst is used with either ethylenediamine alone or ethylenediamine with monoethanolamine at between about 170° C. and about 210° C., the relative amounts of diethylenetriamine and piperazine change over time. FIG. 1 is a graphical representation of the amounts of diethylenetriamine (DETA) and piperazine (PIP) present in a typical reaction mixture over time, as measured by the amount of amine reactants, i.e., ethylenediamine or ethylenediamine and monoethanolamine, converted to product.

It can be seen from the juxtaposition of Curve 1 to Curve 2 that the ratio of DETA to PIP changes over given conversions of the amine reactants. It is therefore possible to optimize the ratio of DETA to PIP for a given catalyst and reaction temperature by limiting to a given conversion.

It is been found in accordance with the present invention that the proper amine reactant conversion point with a catalyst selected from the group of nickel, cobalt and rhodium and a reaction temperature between about 170° C. and 210° C. is less than about 35% and is most preferably less than 25% of the available amine reactants. The reaction temperature chosen between 170° C. and 210° C. is not narrowly critical so long as the reaction time is adjusted to achieve a conversion of less than about 35% of the charged amine reactants. The lower amine reactant conversion of 30% gives a higher average ratio of DETA to PIP. The pressure under which the reactants are maintained is not critical. However, higher pressures lead to lower conversion rates at a given temperature.

The catalysts suitable for use in the practice of the present invention are nickel, cobalt or rhodium catalysts which may be relatively pure metal catalysts or catalysts that have been modified by the addition of molybdenum, chromium, iron or other transition metals in varying amounts. The catalysts may be in a massive form or they may be supported on a carrier such as the preferred silica or alumina carriers wherein the metal is present on the surface of the catalyst in a polyatomic form. Preferred catalysts are Raney nickel and Raney cobalt (available from Davison Chemical) or a Ni/Re/B on silica catalyst prepared as described in U.S. Pat. No. 4,123,462. The catalyst charge, as a weight percent of the total charge, is not narrowly critical, although a charge of about 3% is preferred for the reaction temperatures and times taught herein, as opposed to the 20% catalyst charge as disclosed in British Pat. No. 1,508,460.

The amine composition which is obtained by the practice of the present invention will be a mixture of unreacted ethylenediamine or unreacted ethylenediamine and monoethanolamine, the desired diethylenetriamine, piperazine, and minor amounts of other reaction products such as aminoethylethanolamine, aminoethylpiperazine and higher polyalkylene polyamines. This amine composition may then be distilled to yield the desired diethylenetriamine in a purified form.

The invention will be made more clear by reference to the following examples which are intended to illustrate, but not limit, the scope of the invention.

EXAMPLES

Reaction of Ethylenediamine Alone

EXAMPLE 1

In a one liter, stirred autoclave were placed 10 gm of Raney Nickel #28, active nickel in water (50 mesh), available from Davison Chemical, and 360 gm of ethylenediamine. The reactor was then pressurized to 1000 psia with hydrogen gas and held at 200° C. for 2 hours. Gas chromatographic analysis of the ammonia-free and catalyst-free reaction products, derivatized at 60° C. with N-methyl-bis[trifluoroacetamide], was performed on a ⅛"×18" column of 80/100 mesh HP Chromasorb W coated with 5% OV-225 plus 7.5% polyphenylether [6 ring]. The sample was also analyzed on a ¼"×6' column of Nitro DEGS available under the registered Trademark "Permabond" from HNU Systems, Inc. These analyses revealed that 77% by weight of the ethylenediamine charged remained unconverted and that the product mixture contained 18.2% diethylenetriamine, 1.6% piperazine, 2.4% linear triethylenepentamine, 0.2% aminoethylethanolamine and 0.2% aminoethylpiperazine by weight of the product mixture.

EXAMPLES 2-11

The same procedure as used in Example 1 was used in Examples 2-11 with the changes in catalysts and results indicated in Table I.

TABLE I

| Ex. | Catalyst[1] | Size (micron) | EDA Converted (Mol. %) | Ratio DETA:PIP (wt. %/wt. %) |
|---|---|---|---|---|
| 1 | Nickel #28 | 50 | 23 | 11.4 |
| 2 | Nickel #200 | 20 | 15 | 9.9 |
| 3 | Nickel #4100 | 25 | 16 | 10.3 |
| 4 | Nickel #4200 | 40 | 20 | 10.4 |
| 5 | Cobalt #27 | 50 | 9 | 8.4 |
| 6 | Nickel[2] #2400 | 60 | 9 | 11.5 |
| 7 | Nickel[3] #3000 | 24 | 24 | 8.2 |
| 8 | Nickel[4] #30 | 24 | 29 | 5.1 |
| 9 | Nickel[5] #4300 | 30 | 35 | 4.1 |
| 10 | Rh/Alumina[6] | — | 23 | 6.1 |
| 11 | Ni/Re/B/Silica[7] | — | 23 | 8.9 |
| 12 | Ni/Zr/Support[8] | — | 9 | 3.2 |

[1]Ex. 1-9: Raney nickel and Raney cobalt (active metal in water), available from Davison Chemical
[2]promoted with 2.5% Cr and 1.4% Fe
[3]promoted with 1% Mo
[4]promoted with 2% Mo
[5]promoted with 4-6% Mo
[6].5% rhodium metal supported on alumina from Englehard; size: ⅛" extrudate
[7]prepared per U.S. Pat. No. 4,123,462 with 6.8% Ni, 1.8% Re, 1.4% B on silica; size: ⅛" extrudate
[8]25% Ni on Kieselguhr in oil promoted with 1% Zr; size: 4 mesh from United Catalyst Inc., as #G-70

The foregoing table illustrates that the process of the instant invention yields an amine composition with DETA:PIP ratios ranging from 11.5 to 3.2 at a temperature far outside the ranges described in U.S. Pat. No. 3,714,259 and British Pat. No. 1,508,460.

MONOETHANOLAMINE EXAMPLES 13-19

The procedure of example 1 was repeated in examples 13-19 with the changes in temperature, and catalyst as shown in Table II. The precise charges of amine reactants are also noted in Table II.

TABLE II

| Example | Catalyst | Mole Ratio EDA:MEA | Temp. °C. | Amine Reactants Converted | | | Ratio DETA:PIP (wt. %/wt. %) |
|---|---|---|---|---|---|---|---|
| | | | | EDA, Mol % | MEA Mol % | Total (Mol. %) | |
| 13 | Raney Ni #28[1] | 6:1[4] | 175 | 7 | 3 | 6.4 | 100 |
| 14 | Raney Ni #28 | 6:1 | 200 | 20 | 30 | 21.4 | 8.3 |
| 15 | Ni/Re/B/Silica[2] | 6:1 | 200 | 35 | 42 | 36 | 5.1 |
| 16 | Ni/Re/B/Silica | 6:1 | 170 | 6 | 12 | 6.9 | 16 |
| 17 | Raney Ni #28 | 1:1[5] | 200 | 33 | 23 | 28 | 5.4 |
| 18 | Ni/Re/B/Silica | 1:1 | 200 | 37 | 30 | 33.5 | 3.7 |
| 19 | Ni/Graphite[3] | 6:1 | 200 | 1 | 1 | 2.3 | 0.5 |

[1] For catalyst description, see Ex. 1.
[2] 6.8% Ni, 1.8% Re, 1.4% B on Silica-prepared per U.S. Pat. No. 4,123,462
[3] 10% Ni on graphite, available from Alfa chemical
[4] 360 g EDA and 61 g MEA charged
[5] 180 g EDA and 183 g MEA charged The foregoing table illustrates that the process using monoethanolamine achieves results comparable to the results achieved with the process for reacting ethylenediamine with itself.

Example 19 demonstrates that a graphite support is unsuitable for a nickel catalyst in the practice of the instant invention. This is thought to be caused by the fact that the graphite supported nickel catalyst, Ni Gravimet from Alfa, exposes mainly monoatomic nickel on the catalyst surface.

COMPARATIVE EXAMPLES 20–26

The following examples exemplify the performance of some of the catalysts disclosed in British Pat. No. 1,508,460 and U.S. Pat. No. 3,714,259 along with other known catalysts. The starting material was ethylenediamine and other reaction conditions were as disclosed in example 1.

TABLE III

| Ex. | Catalyst* | Size | EDA Converted (Mol. %) | Ratio DETA:PIP (wt. %/wt. %) |
|---|---|---|---|---|
| 20 | Chromium Powder | — | <2 | 0.6/.2 |
| 21 | Copper Powder #2913 | — | <1 | 0/0 |
| 22 | Fe/Mo #G-105 | 5 mm × 5 mm | 6 | 0/.1 |
| 23 | ZnCr #C70-2 | ¼" × ¼" | <1 | 0/0 |
| 24 | Pd/Cr/Alum #T-370C | ⅛" × ⅛" | 6 | 0/0.2 |
| 25 | Pd/Silica | ⅛" | 5 | 0/0.2 |
| 26 | CuCdCr #T988 | 3/16" × 3/16" | 4 | 0/0 |

*Ex. 20 and 21 - available from Davison Chemical;
Exs. 22–26 - available from United Catalysts, Inc.

The foregoing table demonstrates that many of the catalysts generally disclosed in British Pat. No. 1,508,460 and U.S. Pat. No. 3,714,259 have very low activity under the process conditions of the present invention.

EXAMPLE 27

The procedure of example 1 was repeated with the catalyst of Example 1 which was found to be the most active in the present invention. The temperature was held at 120° C. which is within the range disclosed by British Pat. No. 1,508,460. The reaction mixture was held at 120° C. for 72 hours. At the end of 72 hours gas chromatographic analysis indicated that no reaction had occurred.

I claim:

1. A process for the production of an amine composition containing a high yield ratio of diethylenetriamine to piperazine which comprises maintaining ethylenediamine in the presence of a nickel, cobalt or rhodium catalyst, wherein the metal is present on the surface of the catalyst in a polyatomic form, and at a temperature between about 170° C. to about 210° C. and for a reaction time sufficient to produce diethylenetriamine and convert less than about 35% of the ethylenediamine to polyamine.

2. The process of claim 1 wherein the catalyst is Raney nickel.

3. The process of claim 1 wherein the catalyst is Raney cobalt.

4. The process of claim 1 wherein the catalyst is Ni/Re/B on a silica support.

5. The process of claim 1 wherein the conversion of ethylenediamine is less than about 30%.

6. The process of claim 1 wherein the conversion of ethylenediamine is less than about 25%.

7. A process for the production of an amine composition containing a high yield ratio of diethylenetriamine to piperazine which comprises maintaining a mixture of ethylenediamine and monoethanolamine in the presence of a nickel, cobalt or rhodium catalyst, wherein the metal is present on the surface of the catalyst in a polyatomic form, and at a temperature between about 170° C. and about 210° C. and for a reaction time sufficient to produce diethylenetriamine and convert less than about 35% of the amine reactants to polyamine.

8. The process of claim 7 wherein the catalyst is Raney nickel.

9. The process of claim 7 wherein the catalyst is Raney cobalt.

10. The process of claim 7 wherein the catalyst is Ni/Re/B on a silica support.

11. The process of claim 7 wherein the conversion of amine reactants is less than about 30%.

12. The process of claim 7 wherein the conversion of amine reactants is less than about 25%.

* * * * *